United States Patent
Harada et al.

(10) Patent No.: US 11,206,377 B2
(45) Date of Patent: Dec. 21, 2021

(54) IMAGING APPARATUS, IMAGING SYSTEM, AND IMAGING METHOD

(71) Applicant: OLYMPUS CORPORATION, Tokyo (JP)

(72) Inventors: Yasunari Harada, Ebina (JP); Satoru Adachi, Tsuchiura (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/105,826

(22) Filed: Nov. 27, 2020

(65) Prior Publication Data

US 2021/0105444 A1    Apr. 8, 2021

Related U.S. Application Data (63) Continuation of application No. PCT/JP2019/004881, filed on Feb. 12, 2019.

(30) Foreign Application Priority Data

May 29, 2018 (JP) .............................. JP2018-102608

(51) Int. Cl.
*H04N 7/54* (2006.01)
*H04N 5/225* (2006.01)
*H04N 5/232* (2006.01)

(52) U.S. Cl.
CPC ............... *H04N 7/54* (2013.01); *H04N 5/225* (2013.01); *H04N 5/23203* (2013.01); *H04N 2005/2255* (2013.01)

(58) Field of Classification Search
None
See application file for complete search history.

(56) References Cited

U.S. PATENT DOCUMENTS

2018/0048790 A1*  2/2018  Adachi ................. A61B 1/045
2018/0054580 A1*  2/2018  Adachi ................. H04N 5/3575

FOREIGN PATENT DOCUMENTS

JP     2003-052628 A    2/2003
JP        6138406 B1    5/2017
(Continued)

OTHER PUBLICATIONS

International Search Report dated Apr. 23, 2019 received in PCT/JP2019/004881.

*Primary Examiner* — James M Anderson, II
(74) *Attorney, Agent, or Firm* — Scully, Scott, Murphy & Presser, P.C.

(57) ABSTRACT

An imaging apparatus includes: an imager configured to generate an imaging signal; a transmission channel configured to connect a controller and the images; a superimposed signal generator that is arranged on a proximal end side of the transmission channel, the superimposed signal generator being configured to generate a superimposed signal by superimposing a pulsed data signal and a pulsed reference clock signal, and output the generated superimposed signal to the transmission channel; a first extractor that is arranged on a distal end side of the transmission channel, the first extractor being configured to extract the data signal and the reference clock signal from the generated superimposed signal; and a second extractor that is arranged on the distal end side of the transmission channel, the second extractor being configured to extract the negative voltage from the generated superimposed signal.

15 Claims, 8 Drawing Sheets

(56) References Cited

FOREIGN PATENT DOCUMENTS

| WO | 2017/056536 A1 | 4/2017 |
| WO | 2017/068899 A1 | 4/2017 |

\* cited by examiner

IMAGING APPARATUS, IMAGING SYSTEM, AND IMAGING METHOD

CROSS-REFERENCE TO RELATED APPLICATIONS

This application is a continuation of PCT international application No. PCT/JP2019/004881 filed on Feb. 12, 2019, which designates the United States, incorporated herein by reference, and which claims the benefit of priority from Japanese Patent Application No. 2018-102608, filed on May 29, 2018, incorporated herein by reference.

BACKGROUND

1. Technical Field

The present disclosure relates to an imaging apparatus that is inserted into a subject and generates image data by capturing an in-vivo image of the subject, and relates to an imaging system and an imaging method.

2. Related Art

In the related art, a technology for transmitting a plurality of signals from a processor to an endoscope via a transmission cable in an endoscope system has been known (see Japanese Patent No. 6138406). In this technology, a signal line for transmitting a driving signal for driving an imaging element is eliminated by superimposing a pulse signal for driving the imaging element onto a transmission cable for supplying negative voltage to the imaging element.

SUMMARY

In some embodiments, an imaging apparatus includes: an imager configured to generate an imaging signal by receiving light and performing photoelectric conversion on the light; a transmission channel configured to connect a controller and the imager to transmit the imaging signal, the control device performing image processing on the imaging signal generated by the imager; a superimposed signal generator that is arranged on a proximal end side of the transmission channel, the superimposed signal generator being configured to generate a superimposed signal by superimposing a pulsed data signal that is input from outside and a pulsed reference clock signal that is input from outside on negative voltage that is input from outside, and output the generated superimposed signal to the transmission channel; a first extractor that is arranged on a distal end side of the transmission channel, the first extractor being configured to extract the data signal and the reference clock signal from the generated superimposed signal; and a second extractor that is arranged on the distal end side of the transmission channel, the second extractor being configured to extract the negative voltage from the generated superimposed signal.

In some embodiments, an imaging system includes: an imager configured to generate an imaging signal by receiving light and performing photoelectric conversion on the light; a controller configured to perform image processing on the imaging signal generated by the imager; a transmission channel configured to connect the imager and the controller to transmit the imaging signal; a superimposed signal generator that is arranged on a proximal end side of the transmission channel, the superimposed signal generator being configured to generate a superimposed signal by superimposing a pulsed data signal that is input from outside and a pulsed reference clock signal that is input from outside on negative voltage that is input from outside, and output the generated superimposed signal to the transmission channel; a first extractor that is arranged on a distal end side of the transmission channel, the first extractor being configured to extract the data signal and the reference clock signal from the generated superimposed signal; and a second extractor that is arranged on the distal end side of the transmission channel, the second extractor being configured to extract the negative voltage from the generated superimposed signal.

In some embodiments, an imaging method includes: generating, by an imager, an imaging signal by receiving light and performing photoelectric conversion on the light; performs, by a controller, image processing on the generated imaging signal; transmitting the imaging signal from the imager to the controller; generating, at a proximal end side of a transmission channel, a superimposed signal by superimposing a pulsed data signal that is input from outside and a pulsed reference clock signal that is input from outside on negative voltage that is input from outside; outputting the generated superimposed signal to the transmission channel; extracting, at the distal end side of the transmission channel, the data signal and the reference clock signal from the generated superimposed signal; and extracting, at the distal end side of the transmission channel, the negative voltage from the generated superimposed signal.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for carrying out the present disclosure (hereinafter, referred to as "embodiments") will be described in detail below with reference to the drawings. The present disclosure is not limited by the embodiments below. Further, each of the figures referred to in the description below schematically illustrate shapes, sizes, and positional relationships only to the extent that the contents of the present disclosure can be understood. In other words, the present disclosure is not limited to only the shapes, the sizes, and the positional relationships illustrated in the drawings. Furthermore, in the description below, an endoscope system including a flexible endoscope will be described as an example of the endoscope system.

First Embodiment

Configuration of Endoscope System

Figure 1:
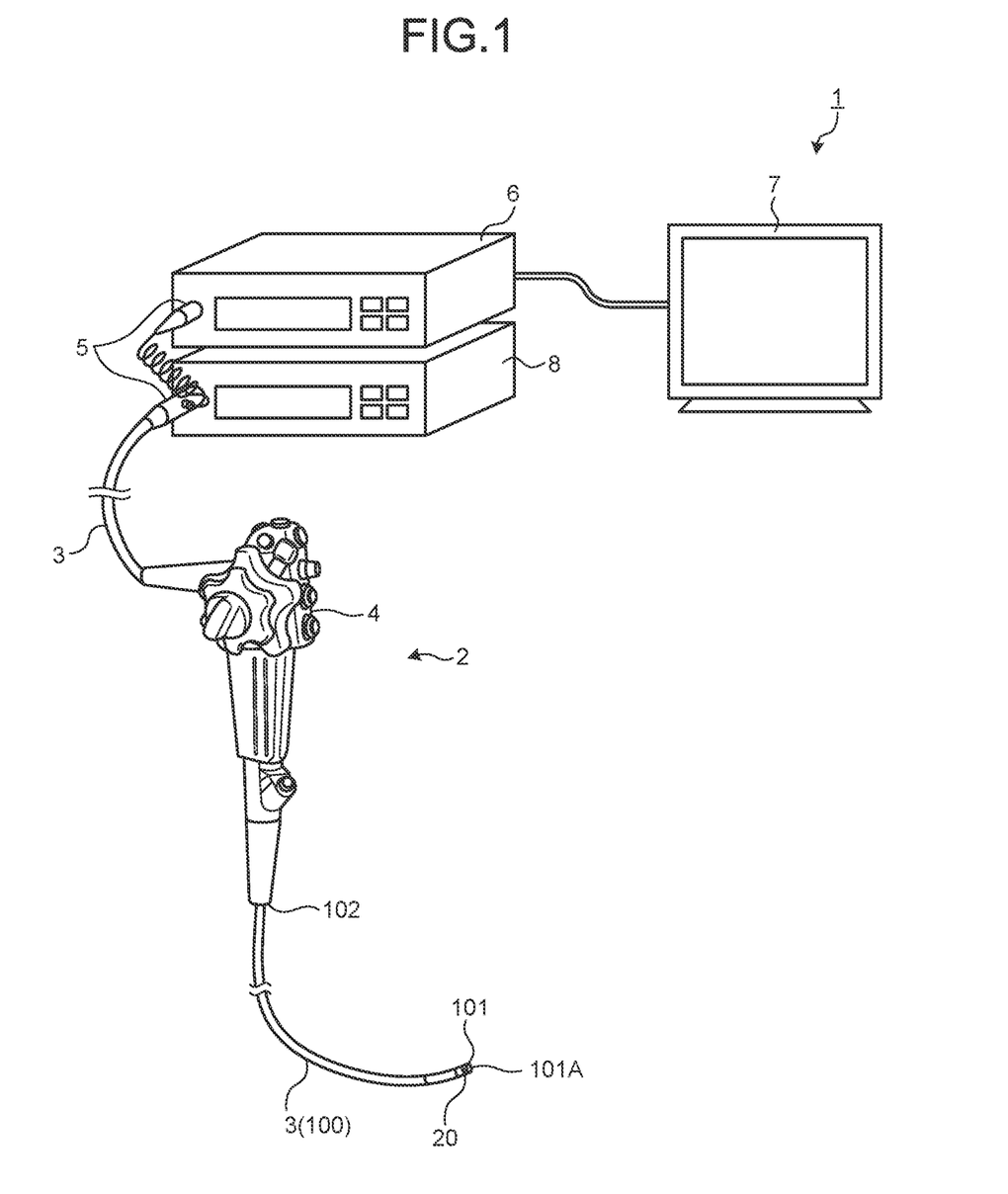
FIG. 1 is an overall diagram schematically illustrating an entire configuration of an endoscope system according to a first embodiment of the present disclosure.

FIG. 1 is an overall diagram schematically illustrating an entire configuration of an endoscope system according to a first embodiment of the present disclosure. An endoscope system 1 illustrated in FIG. 1 includes an endoscope 2, a processor 6 (controller), a display device 7, and a light source device 8.

The endoscope 2 includes a transmission cable 3, an operating unit 4, and a connector unit 5. The endoscope 2 generates an imaging signal by inserting an insertion portion 100 that is a part of the transmission cable 3 into a body cavity of a subject and capturing an image of the inside of the subject, and outputs the imaging signal to the processor 6. The endoscope 2 includes, at one end side of the transmission cable 3 and at a side of a distal end portion 101 of the insertion portion 100 that is inserted into the body cavity of the subject, an imaging unit 20 (imager) that generates an imaging signal by capturing an image of the inside of the body cavity of the subject. Further, the endoscope 2 is connected, at the side of a proximal end 102 of the insertion portion 100, to the operating unit 4 that receives various kinds of operation on the endoscope 2. The imaging signal generated by the imaging unit 20 is output to the connector unit 5 via the transmission cable 3 that has a length of at least 10 centimeters (cm) or longer. The connector unit 5 is removably connected to the processor 6 and the light source device 8, performs predetermined signal processing on the imaging signal output by the imaging unit 20, and outputs the processed imaging signal to the processor 6.

The processor 6 performs predetermined image processing on the imaging signal input from the connector unit 5, outputs the processed imaging signal to the display device 7, and comprehensively controls the entire endoscope system 1.

The display device 7 displays an image corresponding to the imaging signal input from the processor 6, under the control of the processor 6. The display device 7 is configured with an organic electro luminescence (EL), liquid crystal, or the like.

The light source device 8 is configured with, for example, a halogen lamp, a white light emitting diode (LED), or the like. The light source device 8 emits illumination light toward the subject from the distal end portion 101 side of the insertion portion 100 of the endoscope 2 via the connector unit 5 and the transmission cable 3.

Functional Configuration of Main Part of Endoscope System

Figure 2:
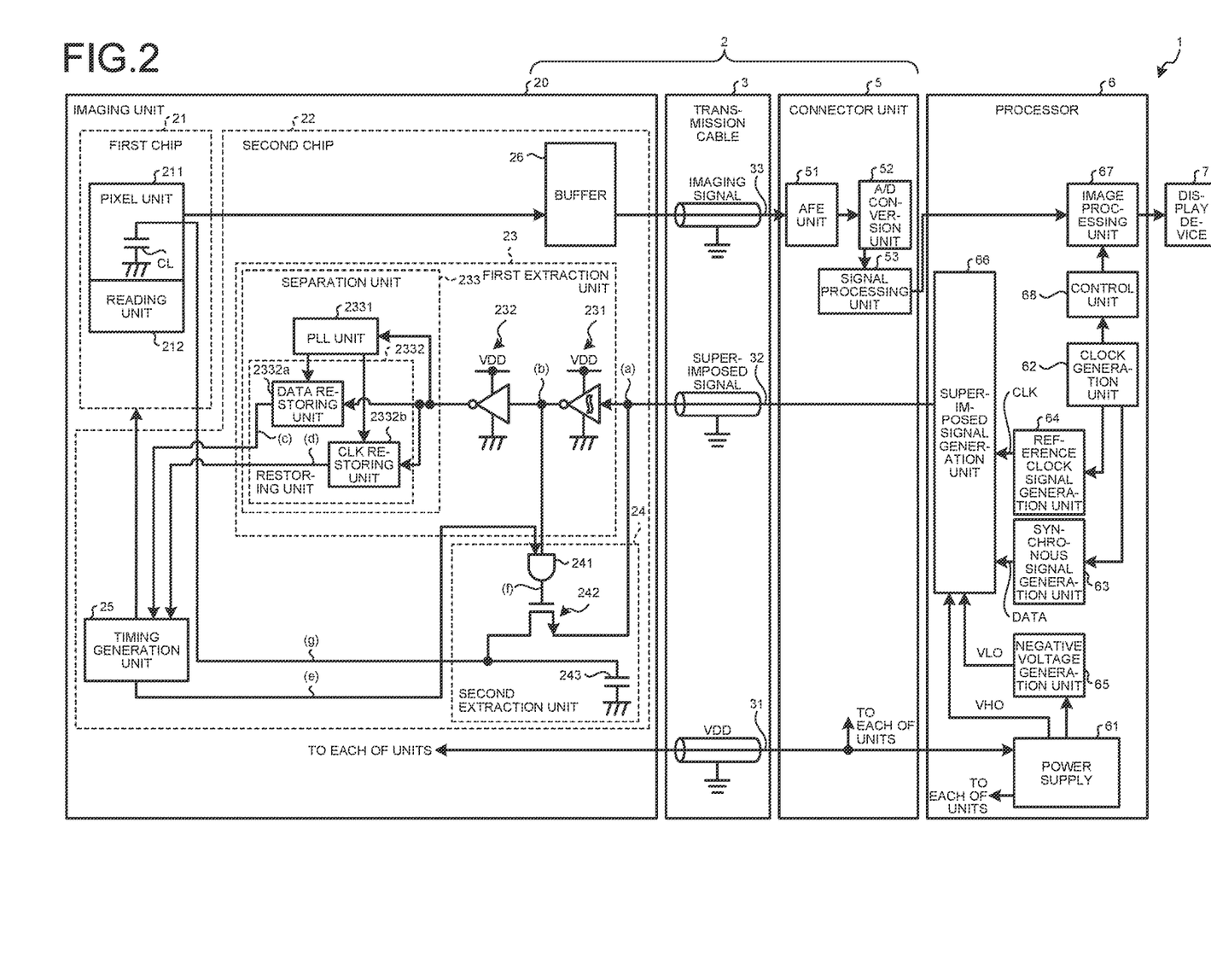
FIG. 2 is a block diagram illustrating a functional configuration of a main part of the endoscope system according to the first embodiment of the present disclosure.

A functional configuration of a main part of the endoscope system 1 as described above will be described below. FIG. 2 is a block diagram illustrating the functional configuration of the main part of the endoscope system 1.

Configuration of Endoscope

First, a configuration of the endoscope 2 will be described.

As illustrated in FIG. 2, the endoscope 2 includes at least the imaging unit 20, the transmission cable 3, and the connector unit 5.

Configuration of Imaging Unit

First, a configuration of the imaging unit 20 will be described.

As illustrated in FIG. 2, the imaging unit 20 generates an imaging signal by receiving light and performing photoelectric conversion on the light. The imaging unit 20 includes at least a first chip 21 and a second chip 22. The first chip 21 and the second chip 22 are semiconductor substrates, in each of which a plurality of functional elements (to be described later) are arranged and which are laminated such that a size in a horizontal planar direction is smaller than 1 cm×1 cm. Further, the imaging unit 20 is arranged parallel to an opening surface 101A of the distal end portion 101 of the endoscope 2.

The first chip 21 includes a pixel unit 211 and a reading unit 212. The pixel unit 211 includes a plurality of pixels 2110 that are arranged in a two-dimensional matrix manner, that receive light from outside, that perform photoelectric conversion to generate imaging signals corresponding to intensity of received light, and that output the imaging signals. The reading unit 212 sequentially selects pixels of the pixel unit 211 row by row, sequentially reads the imaging signals that are accumulated in the pixels, performs predetermined signal processing (for example, correlated double sampling ((DS) or the like) on the sequentially read imaging signals, and outputs the imaging signals to a buffer 26 (to be described later). Meanwhile, in the first embodiment, the first chip 21 functions as an imaging element.

Figure 3:
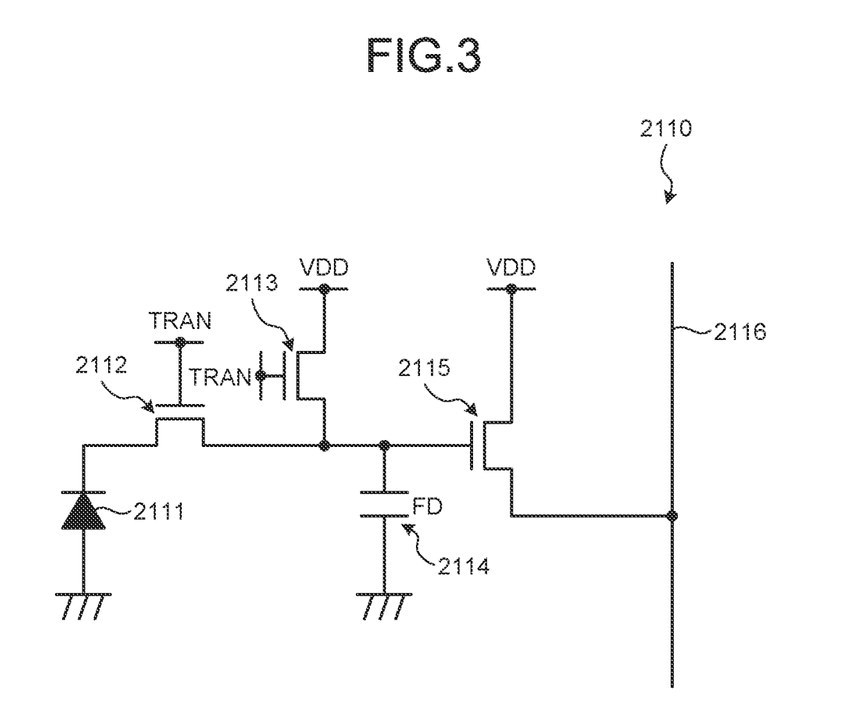
FIG. 3 is a circuit diagram schematically illustrating a configuration of a pixel according to the first embodiment of the present disclosure.

FIG. 3 is a circuit diagram schematically illustrating a configuration of the pixel of the pixel unit 211.

As illustrated in FIG. 3, the pixel 2110 includes a photodiode 2111 (hereinafter, described as the "PD 2111"), a transfer transistor 2112, a reset transistor 2113, a floating diffusion 2114 (hereinafter, referred to as the "FD 2114"), and a pixel output transistor 2115.

The PD 2111 receives incident light, performs photoelectric conversion to a signal charge amount corresponding received light intensity, and accumulates signal charges. A cathode side of the PD 2111 is connected to the transfer transistor 2112, and an anode side is connected to ground GND.

The transfer transistor 2112 transfers the signal charges from the PD 2111 to the FD 2114. A signal line for supplying a transfer signal TRAN is connected to a gate of the transfer transistor 2112, one end side of the transfer transistor 2112 is connected to the PD 2111, and the other end side is connected to the FD 2114. If a voltage level of the transfer signal TRAN reaches a high state, the transfer transistor 2112 enters an ON state and transfers the signal charges from the PD 2111 to the ED 2114. Further, if the voltage level of the transfer signal TRAN reaches a low state, the transfer transistor 2112 enters an OFF state, and the PD 2111 accumulates charges.

The reset transistor 2113 resets the PD 2111 to predetermined potential. One end side of the reset transistor 2113 is connected to power supply voltage VDD, the other end side is connected to the FD 2114, and a gate is connected to a signal line for supplying the transfer signal TRAN. If a voltage level of the transfer signal TRAN reaches a high state, the reset transistor 2113 enters an ON state, discharges the signal charges accumulated in the FD 2114, and resets the FD 2114 to predetermined potential. Further, if the voltage level of the transfer signal TRAN reaches a low state, the reset transistor 2113 enters an OFF state, and the FD 2114 is able to accumulate signal charges. Meanwhile, the voltage level of the transfer signal TRAN in the high state is the power supply voltage VDD, and the voltage level in the low state is negative voltage VLO.

The FD 2114 is constituted of a floating diffusion capacity, and converts the signal charges accumulated in the PD 2111 to voltage.

The pixel output transistor 2115 outputs a signal that has been converted to voltage by the FD 2114 to a vertical transfer line 2116. One end side of the pixel output transistor 2115 is connected to a signal line for supplying the power supply voltage VDD, the other end side is connected to the vertical transfer line 2116, and a gate is connected to the FD 2114.

Referring back to FIG. 2, explanation of the configuration of the imaging unit 20 will be continued.

The second chip 22 includes a first extraction unit 23 (first extractor), a second extraction unit 24 (second extractor), a timing generation unit 25 (timing generator), and the buffer 26.

The first extraction unit 23 is arranged on a distal end side of the transmission cable 3 that serves as a transmission channel, and extracts a reference clock signal CLK and a data signal DATA (SYNC including a vertical synchronous signal and a horizontal synchronous signal) that are included in a superimposed signal input from the processor 6. The first extraction unit 23 includes a first inverter 231, a second inverter 232, and a separation unit 233.

The first inverter 231 is operated by the power supply voltage VDD that is input from the processor 6 via the transmission cable 3, inverts output of the superimposed signal, which is input from the processor 6 via the transmission cable 3, at an input voltage that is intermediate between the power supply voltage VDD and the negative voltage VLO, and outputs the inverted output. The first inverter 231 is configured with a PMOS transistor and an MOS transistor.

The second inverter 232 is operated by the power supply voltage VDD that is input from the processor 6 via the transmission cable 3, inverts output of the superimposed signal, which is input from the first inverter 231, and outputs the inverted output to the separation unit 233.

The separation unit 233 generates and outputs a multiplied clock signal (hereinafter, referred to as a "multiplied CLK"), restores the reference clock signal CLK and the data signal DATA included in the superimposed signal, and outputs the restored reference clock signal CLK and the restored data signal DATA to the timing generation unit 25 (for details of the method, see Japanese Laid-open Patent Publication No. 2017-190429). The separation unit 233 includes a PLL unit 2331 and a restoring unit 2332.

The PLL unit 2331 generates a multiplied CLK with a higher frequency than a frequency of the superimposed signal in synchronization with one of a rising edge and a falling edge of the superimposed signal, and outputs the multiplied CLK to the restoring unit 2332. The PLL unit 2331 includes a phase comparator that compares phases of two input signals and outputs a difference, a charge pump that charges an electric current (or voltage) proportional to the difference, a loop filter that performs smoothing on a pulse signal input from the charge pump, a voltage control oscillator that generates a multiplied CLK by multiplying the frequency of the superimposed signal on the basis of the voltage input from the loop filter, and a frequency divider that performs conversion (performs frequency dividing) to obtain a pulse signal that is reduced to one over integer of the multiplied CLK that has been input from the voltage control oscillator, where the integer is equal to or larger than 1. Meanwhile, in the first embodiment, explanation will be given based on the assumption that the multiple number of the PLL unit 2331 is 1.

The restoring unit 2332 restores, on the basis of the multiplied CLK input from the PLL unit 2331, the reference clock signal CLK and the data signal DATA from the superimposed signal that is input from the second inverter 232, and outputs the restored reference clock signal CLK and the restored data signal DATA to the timing generation unit 25. The restoring unit 2332 includes a data restoring unit 2332a and a CLK restoring unit 2332b.

The data restoring unit 2332a restores, on the basis of the multiplied CLK input from the PLL unit 2331, the data signal DATA from the superimposed signal that is input from the second inverter 232, and outputs the restored data signal DATA to the timing generation unit 25. The data restoring unit 2332a is configured with a quinary counter circuit and a D flip-flop circuit. Specifically, the quinary counter circuit outputs a pulse signal CNT5_OUT corresponding to a fifth rising edge of the multiplied CLK to the D flip-flop circuit, and the D flip-flop circuit latches the superimposed signal at a timing of a rising edge of the fifth multiplied CLK with reference to rising of the superimposed signal, so that the data restoring unit 2332a converts a size of a pulse width to a high state or a low state of a digital signal and restores the data signal DATA.

The CLK restoring unit. 2332b restores, on the basis of the multiplied CLK input from the PLL unit 2331, the reference clock signal CLK from the superimposed signal that is input from the second inverter 232, and outputs the restored reference clock signal CLK to the timing generation unit 25. The CLK restoring unit 2332b is configured with a quinary counter circuit and an RS latch circuit. Specifically, the quinary counter circuit outputs a pulse signal CNT5_OUT corresponding to a fifth rising edge of the multiplied CLK to the RS latch circuit, and the RS latch circuit sets a rising edge of the superimposed signal (high state) and resets the superimposed signal (low state) at the rising edge of the fifth multiplied CLK with reference to a rising position of the superimposed signal, so that the CLK restoring unit 2332b restores the reference clock signal CLK with a constant pulse width.

The second extraction unit 24 is arranged on a distal end side of the transmission cable 3 that serves as a transmission channel, extracts the negative voltage VLO included in the superimposed signal that is input from the processor 6, and outputs the extracted negative voltage VLO to the pixel unit 211. The second extraction unit 24 includes an AND circuit 241, a switch 242, and an external capacitor unit 243.

The AND circuit 241 outputs the superimposed signal, which has been input via the first inverter 231, to the switch 242 on the basis of the signal that is input from the timing generation unit 25. Specifically, if the signal input from the timing generation unit 25 is in the high state, the AND circuit 241 outputs the superimposed signal, which has been input via the first inverter 231, to the switch 242.

The switch 242 is configured with an NMOS, and when the superimposed signal that is input from the AND circuit 241 and that has the voltage level in the high state it to be output, the switch 242 charges negative voltage to the external capacitor unit 213. Further, if the superimposed signal that is input from the AND circuit 241 and that has the voltage level in the low state is to be output, the switch 242 maintains charges in the external capacitor unit 243.

The external capacitor unit 243 is configured with a capacitor or the like, and holds the negative voltage VLO that is input via the switch 242.

The timing generation unit 25 generates a driving signal for driving the pixel unit 211 on the basis of the reference clock signal CLK and the data signal DATA input from the first extraction unit 23, and outputs the driving signal to the pixel unit 211. Further, the timing generation unit 25 controls operation of the second extraction unit 24 on the basis of the reference clock signal CLK and the data signal DATA that are input from the separation unit 233. Specifically, the timing generation unit 25 outputs voltage at a high level to the AND circuit 241 during a blanking period of the pixel unit 211, on the basis of the reference clock signal CLK and the data signal DATA (SYNC) that are input from the separation unit 233. The timing generation unit 25 is configured with a timing generator or the like.

The buffer 26 amplifies the analog imaging signal input from the pixel unit 211 in the first chip 21, and outputs the amplified analog imaging signal to the transmission cable 3.

Configuration of Transmission Cable

A configuration of the transmission cable 3 will be described below.

The transmission cable 3 is configured with a plurality of signal lines and a light guide (not illustrated). Specifically, the transmission cable 3 includes at least a signal line 31 for transmitting the power supply voltage VDD, a signal line 32 for transmitting the superimposed signal, and a signal line 33 for transmitting the imaging signal. Meanwhile, in the first embodiment, the transmission cable 3 functions as a transmission channel.

Configuration of Connector Unit

A configuration of the connector unit 5 will be described below.

The connector unit 5 includes an analog front end unit (hereinafter, simply referred to as the "AFE unit 51"), an analog-to-digital (A/D) conversion unit 52, and a signal processing unit 53.

The AFE unit 51 receives the imaging signal input from the signal line 33 of the transmission cable 3, performs impedance matching using a passive component, such as a resistance, subsequently extracts an alternating-current component using a capacitor, and determines an operation point by a partial pressure resistance. Thereafter, the AFE unit 51 amplifies the imaging signal (analog signal) and outputs the amplified imaging signal to the A/D conversion unit 52.

The A/D conversion unit 52 converts the analog imaging signal input from the AFE unit 51 to a digital imaging signal, and outputs the digital imaging signal to the final processing unit 53.

The signal processing unit 3 performs signal processing, such as a noise removal process and a format conversion process, on the digital imaging signal input from the A/D conversion unit 52, and outputs the processed digital imaging signal to the processor 6.

Configuration of Processor

A configuration of the processor 6 will be described below.

The processor 6 includes a power supply 61, a clock generation unit 62, a synchronous signal generation unit 63, a reference clock signal generation unit 64, a negative voltage generation unit 65, a superimposed signal generation unit 66 (superimposed signal generator), an image processing unit 67, and a control unit 68.

The power supply 61 generates the power supply voltage VDD on the basis of electric power input from outside, and outputs the generated power supply voltage VDD together with the ground GND to the imaging unit 20 and the connector unit 5 via the signal line 31 of the transmission cable 3 and a jacket of the signal line 31. Further, the power supply 61 outputs the power supply voltage VDD to each of the units of the processor 6, and outputs positive voltage VHO (High=VDD) to the superimposed signal generation unit 66.

The clock generation unit 62 generates a clock signal that serves as a reference of operation of each of the components of the endoscope system 1, and outputs the clock signal to the synchronous signal generation unit 63, the reference clock signal generation unit 64, and the control unit 68. The clock generation unit 62 is configured with a clock module.

The synchronous signal generation unit 63 generates a pulsed data signal DATA (including a vertical synchronous signal, a horizontal synchronous signal, and a control signal) on the basis of the clock signal that is input from the clock generation unit 62, and outputs the generated data signal DATA to the superimposed signal generation unit 66. The data signal DATA includes the vertical synchronous signal, the horizontal synchronous signal, and the control signal directed to the imaging unit 20. Meanwhile, in the first embodiment, the synchronous signal generation unit 63 functions as a data signal generation unit.

The reference clock signal generation unit 64 generates a pulsed reference clock signal CLK on the basis of the clock signal that is input from the clock generation unit 62, and outputs the pulsed reference clock signal CLK to the superimposed signal generation unit 66 of the processor 6.

The negative voltage generation unit 65 generates negative voltage VLO (−1V), and outputs the negative voltage VLO to the superimposed signal generation unit 66.

The superimposed signal generation unit 66 is arranged on a proximal end side of the transmission cable 3. The superimposed signal generation unit 66 generates a superimposed signal by superimposing the negative voltage VLO, the positive voltage VHO, the synchronous signal SYNC that is input from the synchronous signal generation unit 63, and the reference clock signal CLK that is input from the reference clock signal generation unit 64, and outputs the superimposed signal to the transmission cable 3. Specifically, the superimposed signal generation unit 66 generates the superimposed signal by converting each of the high state and the low state of the voltage level of the data signal DATA to a voltage level of the power supply voltage VHO (VDD) and a voltage level of the negative voltage VLO, and associating the high state and the low state of the voltage level of the data signal DATA with a change of a pulse width of the reference clock signal CLK. For example, the superimposed signal generation unit 66 generates, as the superimposed signal, a signal for which the high state and the low state of the voltage level of the data signal DATA is converted to a size of the pulse width of the reference clock signal CLK, a signal for which the low state of the voltage level is the negative voltage VLO (−1V) and the high state of the voltage level is the positive voltage VHO (VDD), and a signal for which the high state and the low state of the voltage level of the data signal DATA are associated with a change of the pulse width of the reference clock signal CLK.

The image processing unit 67 performs predetermined image processing on the digital imaging signal that is input from the connector unit 5, and outputs the processed digital imaging signal to the display device 7. Here, examples of the predetermined image processing include a while balance adjustment process and a demosaicing process.

The control unit 68 comprehensively controls each of the units of the endoscope system 1. The control unit 68 is configured with a central processing unit (CPU) or the like.

Characteristics of First Inverter

Characteristics of the first inverter 231 will be described below.

Figure 4:
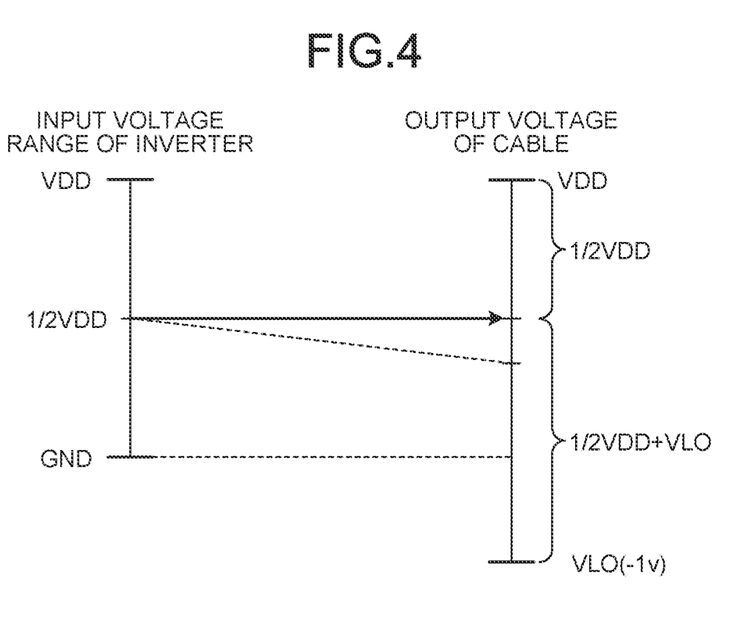
FIG. 4 is a diagram for schematically explaining a relationship between input voltage of a first inverter and output voltage according to the first embodiment of the present disclosure.

FIG. 4 is a diagram for schematically explaining a relationship between input voltage of the first inverter 231 and output voltage.

As illustrated in FIG. 4, in the first inverter 231, an input voltage ranges from the power supply voltage VDD to the ground GND, and a logical threshold for inverting output at an input voltage (1/2VDD) that is intermediate between the power supply voltage VDD and the ground GND is set. In contrast, an output voltage of the signal line 32 of the transmission cable 3 ranges from the power supply voltage VDD to the negative voltage VLO (−1V), so that an intermediate voltage value is different from that of the first inverter 231. Therefore, the first inverter 231 sets a channel width. (W) on the basis of a voltage value (voltage level) of the power supply voltage VDD for driving the first inverter 231 and a voltage value (voltage level) of a negative voltage superimposed on the superimposed signal. Specifically, if the logical threshold is set to ½ of the input voltage range of the first inverter 231 (VDD×(½)), the first inverter 231 sets the logical threshold such channel widths of the PMOS transistor and the NMOS transistor satisfy Expression (1) below.

$$\mu_p W_p = \mu_n W_n \frac{\left(\frac{1}{2}VDD - VLO - V_{Tn}\right)^2}{\left(\frac{1}{2}VDD - V_{Tp}\right)^2} \quad (1)$$

Here, $\mu_p$ represents mobility of electron in the PMOS transistor, $W_p$ represents a gate width, $V_{Tp}$ represents threshold voltage, $\mu_n$ represents mobility of electron in the NMOS transistor, $W_n$ represents a gate width, and $V_{Tn}$ represents threshold voltage.

Operation of Endoscope System

Operation of each of the units of the endoscope system will be described below.

Figure 5:
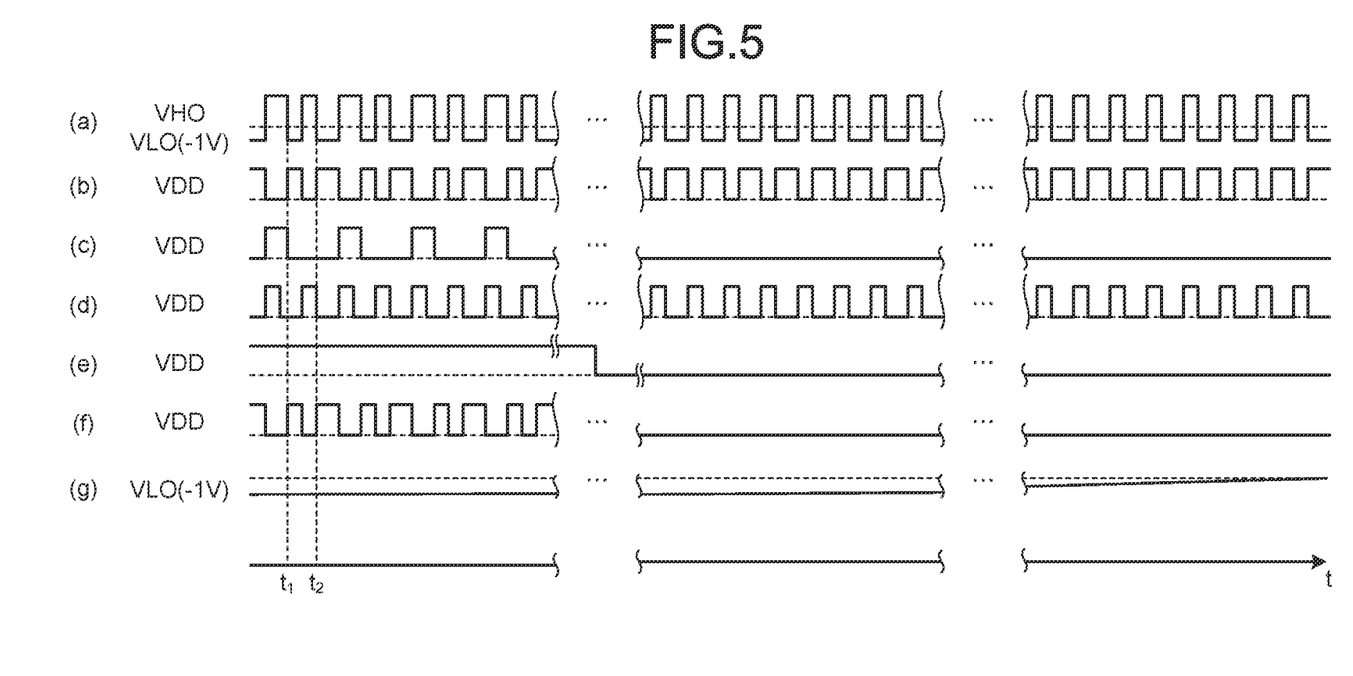
FIG. 5 is a timing diagram schematically illustrating operation of the endoscope system according to the first embodiment of the present disclosure.

FIG. 5 is a diagram schematically illustrating a timing diagram of operation of each of the units of the endoscope system 1. In FIG. 5, (a) to (g) from the top indicates signals (a) to (g) illustrated in FIG. 2. Specifically, from the top in FIG. 5, (a) indicates the superimposed signal, (b) indicates the inverted superimposed signal, (c) indicates the synchronous signal SYNC, (d) indicates the reference clock signal CLK, (e) indicates the control signal, (f) indicates a control signal of the switch 242, and (g) indicates a voltage state of the external capacitor unit 243.

As illustrated in (a) of FIG. 5, the first inverter 231 inverts output of the superimposed signal at the input voltage that is intermediate between the power supply voltage VDD and the negative voltage VLO, and outputs the inverted superimposed signal (see (b) of FIG. 5).

Further, as illustrated in (c) of FIG. 5, the data restoring unit 2332*a* restores the data signal DATA from the superimposed signal that is input from the second inverter 232, on the basis of the multiplied CLK (not illustrated) that is input from the PLL unit 2331.

Furthermore, as illustrated in (d) of FIG. 5, the CLK restoring unit 2332*b* restores the reference clock signal CLK from the superimposed signal that is input from the second inverter 232, on the basis of the multiplied CLK that is (not illustrated) input from the PLL unit 2331.

Moreover, as illustrated in (f) of FIG. 5, the control signal with the voltage level in the high state is input from the timing generation unit 25 to the switch 242 during the blanking period of the pixel unit 211 (see (e) of FIG. 5), under the control of the timing generation unit 25. In this case, when the superimposed signal that is input from the AND circuit 241 and that has the voltage level in the high state is output at a timing at which the negative voltage is input from the first inverter 231 (for example, a time t1, a time t2, and the like), the switch 242 enters the ON state and the switch 242 charges the negative voltage to the external capacitor unit 243 (see (g) of FIG. 5). Accordingly, the negative voltage is charged to the external capacitor unit 243. Thereafter, the external capacitor unit 243 supplies the negative voltage to the pixel unit 211 after the blanking period of the pixel unit 211 ends (see (e) of FIG. 5). Therefore, the negative voltage charged to the external capacitor unit 243 gradually changes to the ground GND due to the effect of leak current or the like in the pixel unit 211 (see (g) of FIG. 5).

According to the first embodiment as described above, the superimposed signal generation unit 66 generates the superimposed signal by superimposing the data signal DATA and the reference clock signal CLK on the negative voltage VLO, and outputs the superimposed signal to the signal line 32 of the transmission cable 3, so that it is possible to transmit three kinds of signals by using a single line to the imaging unit 20, and it is possible to further reduce the number of transmission cables.

Furthermore, according to the first embodiment, the superimposed signal generation unit 66 generates the superimposed signal by converting each of the high state and the low state of the voltage level of the data signal DATA to the voltage level of the power supply voltage VDD and the voltage level of the negative voltage VLO and associating the high state and the low state of the voltage level of the data signal DATA with a change of the pulse width of the reference clock signal CLK, so that it is possible to eliminate a signal line for transmitting the negative voltage VLO from a conventional transmission cable.

Moreover, according to the first embodiment, the channel width of the first inverter 231 is set based on the voltage level of the power supply voltage VDD and the voltage level of the negative voltage VLO, and the superimposed signal that has been input via the transmission cable 3 is output after the voltage level is inverted, so that it is possible to increase the output voltage range of the transmission cable 3 and prevent jitter at the edge of the superimposed signal.

Furthermore, according to the first embodiment, the negative voltage VLO is charged to the external capacitor unit 243 and the negative voltage VLO is supplied to the pixel unit 211, so that it is possible to improve image quality.

Moreover, according to the first embodiment, the timing generation unit 25 charges the negative voltage VLO to the external capacitor unit 243 by driving the switch 242 during the blanking period of the imaging unit 20, so that it is possible to reduce an influence of noise that may be superimposed on a video signal.

Furthermore, according to the first embodiment, the frequency at one of the edges of the superimposed signal stabilized, so that it is possible to reduce a size of a device as compared to a PLL circuit that restores the reference clock signal CLK from a superimposed signal that is transmitted by a clock embedded system.

Moreover, according to the first embodiment, the restoring unit 2332 restores the reference clock signal CLK and the data signal DATA from the superimposed signal for which the frequency at one of the rising edge and the falling edge is stabilized, so that it is possible to reduce a size of a device as compared to the PLL circuit that restores the reference clock signal CLK from the superimposed signal.

Furthermore, according to the first embodiment, the imaging unit 20 is arranged parallel to the opening surface 101A of the distal end portion 101 of the endoscope 2, so that it is possible to reduce a rigid length in the distal end portion 101 of the endoscope 2, reduce a size of the imaging unit 20, and reduce a diameter.

Meanwhile, in the first embodiment, the superimposed signal generation unit 66 is arranged in the processor 6, but embodiments are not limited thereto, and the superimposed signal generation unit 66 may be arranged in, for example, the connector unit 5.

Modification of First Embodiment

A modification of the first embodiment will be described below. In the first embodiment as described above, the analog imaging signal is transmitted; however, in the modification of the first embodiment, a digital imaging signal is transmitted. In the following description, the same components as those of the endoscope system 1 according to the first embodiment will be denoted by the same reference symbols, and detailed explanation thereof will be omitted.

Functional Configuration of Main Part of Endoscope System

Figure 6:
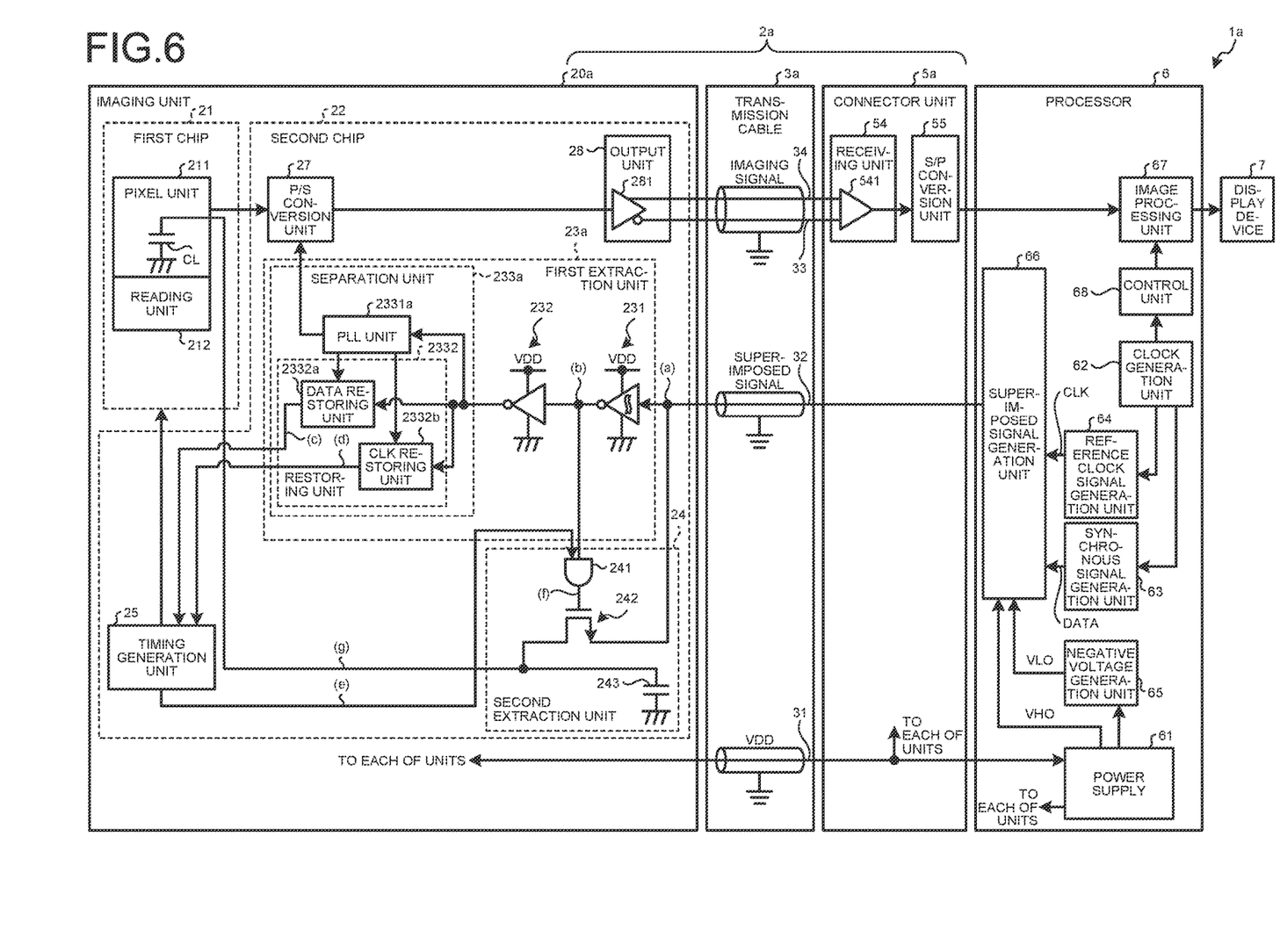
FIG. 6 is a block diagram illustrating a functional configuration of a main part of an endoscope system according to a modification of the first embodiment of the present disclosure.

FIG. 6 is a block diagram illustrating a functional configuration of a main part of an endoscope system according to the modification of the first embodiment. An endoscope system 1a illustrated in FIG. 6 includes an endoscope 2a instead of the endoscope 2 of the endoscope system 1 according to the first embodiment as described above.

Configuration of Endoscope

The endoscope 2a illustrated in FIG. 6 includes ac imaging unit 20a, a transmission cable 3a, and a connector unit 5a.

Configuration of Imaging Unit

First, a configuration of the imaging unit 20a will be described.

The imaging unit 20a illustrated in FIG. 6 includes a first extraction unit 23a instead of the first extraction unit 23 of the first embodiment as described above. Further, the imaging unit 20a includes a P/S conversion unit 27 (parallel-to-serial converter) and an output unit 28 instead of the buffer 26.

The first extraction unit 23a includes a separation unit 233a instead of the separation unit 233 of the first embodiment as described above. The separation unit 233a includes a PLL unit 2331a instead of the PLL unit 2331 of the first embodiment as described above. The PLL unit 2331a generates a multiplied CLK with a higher frequency than the frequency of the superimposed signal in synchronization with one of the rising edge and the falling edge of the superimposed signal, and outputs the multiplied CLK to the P/S conversion unit 27. Specifically, the PLL unit 2331a generates the multiplied CLK by more than doubling the frequency of the superimposed signal in synchronization with one of the rising edge and the falling edge of the superimposed signal that is input from the second inverter 232, and outputs the multiplied CLK to the P/S conversion unit 27 and the restoring unit 2332. The PLL unit 2331a includes a phase comparator that compares phases of two input signals and outputs a difference, a charge pump that charges an electric current (or voltage) proportional to the difference, a loop filter that performs smoothing on a pulse signal input from the charge pump, a voltage control oscillator that generates a multiplied. CLK by multiplying the frequency of the superimposed signal on the basis of the voltage input from the loop filter, a frequency divider that performs conversion (performs frequency dividing) to obtain a pulse signal that is reduced to one over integer of the multiplied CLK that has been input from the voltage control oscillator, where the integer is equal to or larger than 1. Meanwhile, in the modification of the first embodiment, explanation will be given based on the assumption that the multiple number of the PLL unit 2331 is 10.

The P/S conversion unit 27 performs parallel-to-serial conversion on the imaging signal, which has been input from the pixel unit 211, to obtain serial data on the basis of the multiplied CLK that is input from the first extraction unit 23a, and outputs the converted serial data to the output unit 28.

The output unit 28 outputs an imaging signal of the serial data, which is input from the P/S conversion unit 27, to the connector unit 5a via two signal lines 33 and 34 in the transmission cable 3 (to be described later) by low voltage differential signaling (LVDS). The output unit 28 includes a difference amplifier 281 that outputs the imaging signal of the serial data, which is input from the P/S conversion unit 27, via the two signal lines 33 and 34. Meanwhile, in the modification of the first embodiment, the output unit 28 outputs, by LVDS, the imaging signal of the serial data input from the P/S conversion unit 27 to the two signal lines 33 and 34, but embodiments are not limited to this example, and it may be possible to output the imaging signal to the connector unit 5a by superimposing the imaging signal on a different signal line, or by using a different method.

Configuration of Transmission Cable

A configuration of the transmission cable 3a will be described below.

The transmission cable 3a is configured with a plurality of signal lines and a light guide (not illustrated). Specifically, the transmission cable 3a includes at least the signal line 31 for transmitting the power supply voltage VDD, the signal line 32 for transmitting the superimposed signal, and the signal lines 33 and 34 for transmitting the imaging signal by LVDS.

Configuration of Connector Unit

A configuration of the connector unit 5a will be described below.

The connector unit 5a includes a receiving unit 54 and an S/P conversion unit 55.

The receiving unit 54 receives the imaging signal that is transmitted via the signal lines 33 and 34 of the transmission cable 3, and outputs the imaging signal to the S/P conversion unit 55. The receiving unit 54 includes a reception amplifier 541 that receives the imaging signal that is transmitted via the signal lines 33 and 34 of the transmission cable 3.

The S/P conversion unit 55 performs serial-to-parallel conversion on the imaging signal that is input from the receiving unit 54, and outputs the converted imaging signal to the image processing unit 67 of the processor 6.

According to the modification of the first embodiment as described above, the PLL unit 2331 generates the multiplied CLK that has a higher frequency than the frequency of the superimposed signal and that is used to drive the P/S conversion unit 27, in synchronization with one of the rising edge and the falling edge of the superimposed signal, so that it is possible to increase a transmission speed of the imaging signal and reduce the number of lines in the distal end portion 101 simultaneously.

Second Embodiment

A second embodiment will be described below. In the second embodiment, a multiplier unit that multiplies load capacity of the pixel unit 211 is provided to eliminate the external capacitor unit 243 of the first embodiment as described above. Therefore, in the following, a configuration of the endoscope system according to the second embodiment will be described. Meanwhile, the same components as those of the endoscope system 1 according to the first embodiment as described above will be denoted by the same reference symbols, and detailed explanation thereof will be omitted.

Configuration of Endoscope System

Figure 7:
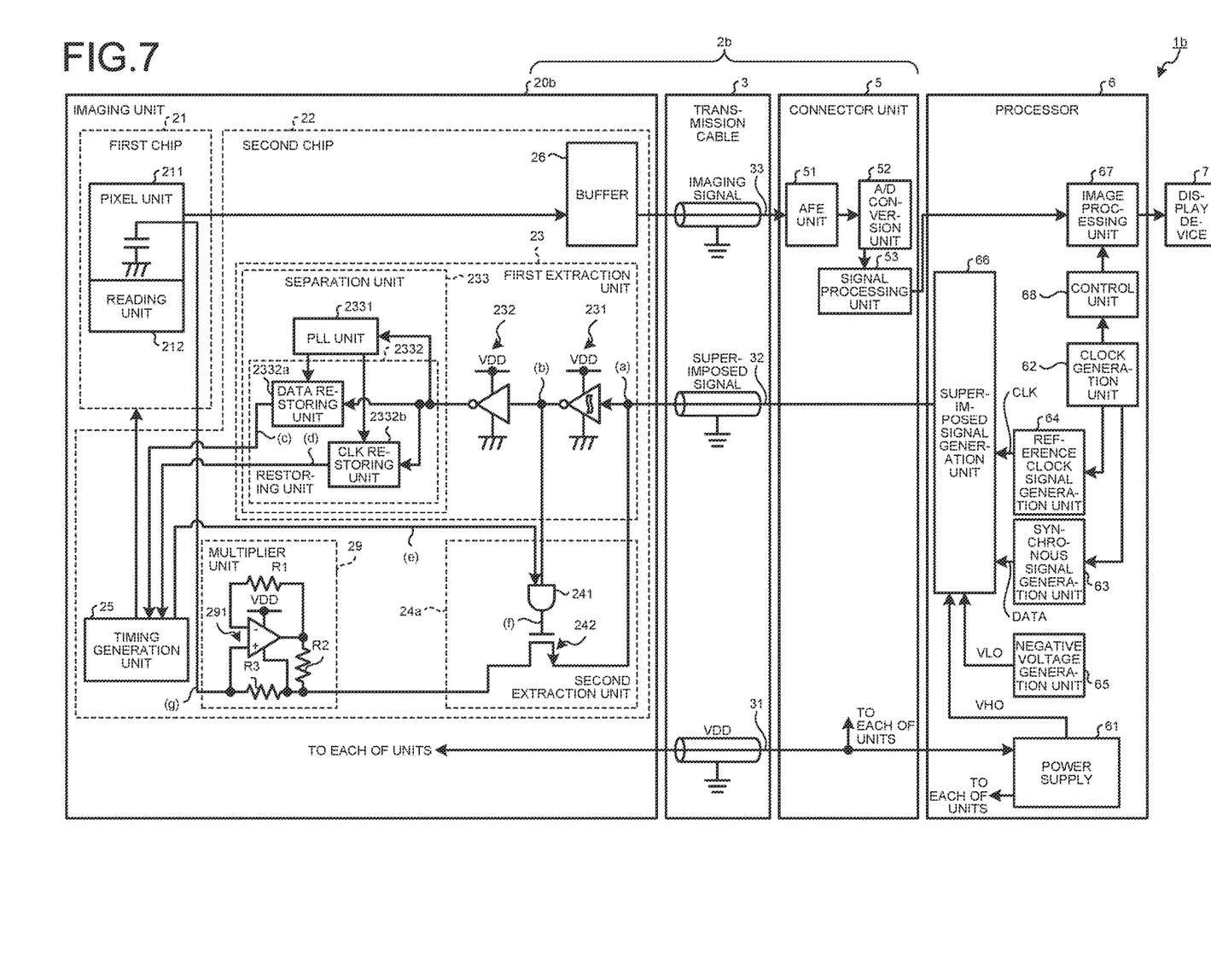
FIG. 7 is a block diagram illustrating a functional configuration of a main part of as endoscope system according to a second embodiment of the present disclosure.

FIG. 7 is a block diagram illustrating a functional configuration of a main part of the endoscope system according to the second embodiment. An endoscope system 1b illustrated in FIG. 7 includes an endoscope 2b instead of the endoscope 2 according to the first embodiment as described above.

Configuration of Endoscope

A configuration of the endoscope 2b will be described. As illustrated in FIG. 7, the endoscope 2b includes an imaging unit 20b instead of the imaging unit 20 of the first embodiment as described above. The imaging unit 20b includes a second extraction unit 24a instead of the second extraction unit 24 of the first embodiment as described above. Further, the imaging unit 20b includes a multiplier unit 29. The second extraction unit 24a is configured by removing the external capacitor unit 243 from the configuration of the second extraction unit 24 of the first embodiment as described above.

The multiplier unit. 29 is electrically connected between an output terminal of the switch 242 and the pixel unit 211, and multiplies the load capacity of the pixel unit 211. The multiplier unit 29 supplies the negative voltage VLO input from to the pixel unit 211. The multiplier unit 29 includes an operation amplifier 291, a first resistance R1, a second resistance R2, and a third resistance R3.

The operation amplifier 291 includes a positive input terminal, a negative input terminal, and an output terminal. One end of the first resistance R1 is electrically connected to the negative input terminal of the operation amplifier 291, and the other end is electrically connected to the output terminal of the operation amplifier 291. One end of the second resistance R2 is electrically connected to the output terminal of the operation amplifier 291, and the other end is electrically connected to the output terminal of the switch 242 and the third resistance R3. One end of the third resistance R3 is electrically connected to the positive input terminal and the pixel unit 211, and the other end is connected to the second resistance R1.

If the third resistance R3 is equal to the first resistance R1, the multiplier unit 29 configured as described above multiplies with respect to the negative voltage VLO by Expression (2) below.

$$C_{Total} = CL \times (R3/R2) \quad (2)$$

Here, CL represents synthetic capacity of all of transistors of the pixel unit 211 that is connected to the multiplier unit 29.

According to the second embodiment as descried above, by arranging the multiplier unit 29, it is possible to eliminate the external capacitor unit 243 of the first embodiment as described above, so that it is possible to further reduce the size of the imaging unit 20b.

Modification of Second Embodiment

A modification of the second embodiment will be described below. In the second embodiment as described above, the analog imaging signal is transmitted; however, is the modification of the second embodiment, a digital imaging signal is transmitted. In the following, the same components as those of the endoscope systems 1 and 1b of the first and the second embodiments are denoted by the same reference symbols, and detailed explanation thereof will be omitted.

Functional Configuration of Main Part of Endoscope System

Figure 8:
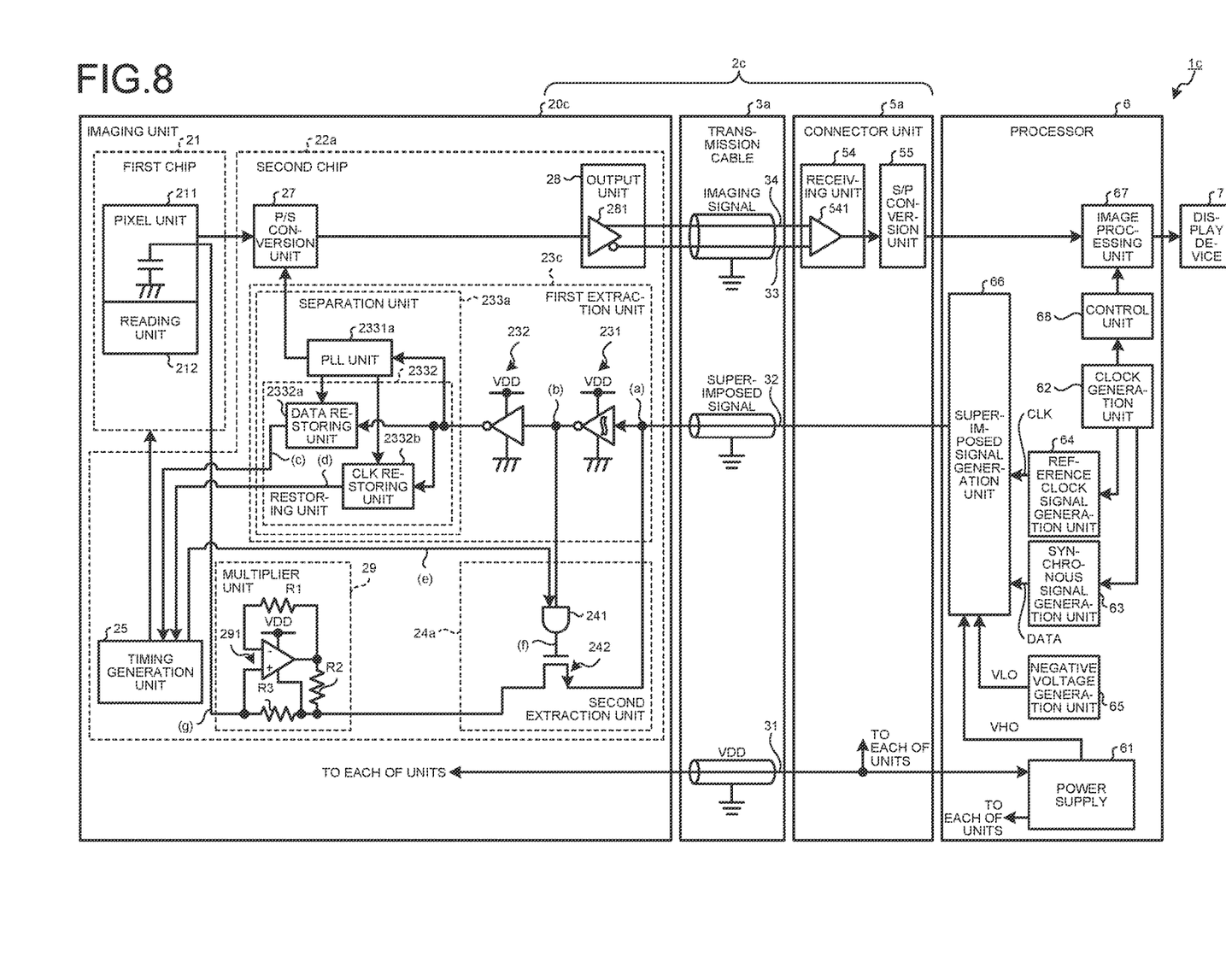
FIG. 8 is a block diagram illustrating a functional configuration of a main part of an endoscope system according to a modification of the second embodiment of the present disclosure.

FIG. 8 is a block diagram illustrating a functional configuration of a main part of an endoscope system according to the modification of the second embodiment. An endoscope system 1c illustrated in FIG. 8 includes an endoscope 2c instead of the endoscope 2b of the endoscope system 1b of the second embodiment as described above.

Configuration of Endoscope

The endoscope 2c illustrated in FIG. 8 includes an imaging unit 20c, the transmission cable 3a, and the connector unit 5a.

Configuration of Imaging Unit

The imaging unit 20c includes a first extraction unit 23c instead of a first extraction unit 23b of the second embodiment as described above. Further, the imaging unit 20c includes the P/S conversion unit 27 and the output unit 28 of the modification of the First embodiment as described above, instead of the buffer 26.

The first extraction unit. 23c includes the separation unit 233a of the modification of the first embodiment as described above, instead of the separation unit 233 of the second embodiment as described above.

According to the modification of the second embodiment as described above, it is possible to eliminate the external capacitor unit 243 of the modification of the first embodiment as described above, so that it is possible to further reduce the size of the imaging unit 20c.

Other Embodiments

Various embodiments may be made by appropriately combining a plurality of constituent elements disclosed in the first and the second embodiments and the modifications as described above. For example, some constituent elements may be deleted from all of the constituent elements described in the first and the second embodiments and the modifications as described above. Furthermore, the constituent elements described in the first and the second embodiments and the modifications may be appropriately combined.

Moreover, in the first and the second embodiments and the modifications, the controller and the light source device are separated, but they may be configured in an integrated manner.

Furthermore, in the first and the second embodiments and the modifications, the endoscope system including the flexible endoscope is described, but it may be possible to adopt an endoscope system including a rigid endoscope and an endoscope system including an industry endoscope.

Moreover, in the first and the second embodiments and the modifications, the endoscope system including an endoscope that is inserted into a subject is described, but it may be possible to adopt, for example, an endoscope system including a rigid endoscope or an endoscope system including a nasal endoscope and an electric scalpel, an inspection probe, or the like.

Furthermore, in the first and the second embodiments and the modifications, the "unit" described above may be replaced with a "means", a "circuit", or the like. For example, the control unit may be replaced with a control means or a control circuit.

In describing the flowcharts in the present specification, context of the processes among the steps is disclosed by using expressions, such as "first", "thereafter", and "subsequently", but the sequences of the processes necessary for carrying out the present disclosure are not uniquely defined by these expressions. In other words, the sequences of the processes in the timing diagrams described in the present specification may be modified as long as there is no contradiction.

According to the present disclosure, it is possible to reduce the number of lines in a transmission cable.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging apparatus comprising:
   an imager configured to generate an imaging signal by receiving light and performing photoelectric conversion on the light;
   a transmission channel configured to connect a controller and the imager to transmit the imaging signal, the controller performing image processing on the imaging signal generated by the imager;
   a superimposed signal generator that is arranged on a proximal end side of the transmission channel, the superimposed signal generator being configured to generate a superimposed signal by superimposing a pulsed data signal that is input from outside and a pulsed reference clock signal that is input from outside on negative voltage that is input from outside, and output the generated superimposed signal to the transmission channel;
   a first extractor that is arranged on a distal end side of the transmission channel, the first extractor being configured to extract the pulsed data signal and the pulsed reference clock signal from the generated superimposed signal; and
   a second extractor that is arranged on the distal end side of the transmission channel, the second extractor being configured to extract the negative voltage from the generated superimposed signal.

2. The imaging apparatus according to claim 1,
   wherein the superimposed signal generator is configured to:
   convert a high state and a low state of a voltage level of the pulsed data signal to a voltage level of power supply voltage that is input from outside and a voltage level of the negative voltage, respectively, and
   generate the superimposed signal by associating the high state and the low state of the voltage level of the pulsed data signal with a change of a pulse width of the pulsed reference clock signal.

3. The imaging apparatus according to claim 2,
   wherein the first extractor includes an inverter configured to operate at the power supply voltage,
   wherein the inverter has a channel width that is set based on the voltage level of the power supply voltage and the voltage level of the negative voltage, and
   wherein the inverter is configured to invert a voltage level of the superimposed signal that is input via the transmission channel to output the superimposed signal having the inverted voltage signal.

4. The imaging apparatus according to claim 3,
   wherein the second extractor comprises:
   an external capacitor configured to be charged with the negative voltage; and
   a switch configured to connect the external capacitor and the inverter, and
   wherein, if the voltage level of the superimposed signal is in a low state, the external capacitor is configured to be charged with the negative voltage via the switch and supply the negative voltage to the imager.

5. The imaging apparatus according to claim 4, further comprising:
   a timing generator that is arranged on the distal end side of the transmission channel, the timing generator being configured to control drive of each of the switch and the imager based on the pulsed data signal and the pulsed reference clock signal that are extracted by the first extractor.

6. The imaging apparatus according to claim 5,
   wherein the timing generator is configured to charge the negative voltage to the external capacitor by driving the switch during a blanking period of the imager.

7. The imaging apparatus according to claim 4, further comprising:
   a multiplier that is electrically connected between an output terminal of the switch and the imager, the multiplier being configured to multiply load capacity of the imager,
   wherein the negative voltage that is input via the switch and the multiplier is supplied to the imager.

8. The imaging apparatus according to claim 7,
   wherein the multiplier comprises
   an operation amplifier comprising a positive input terminal, a negative input terminal, and an output terminal;
   a first resistance that has one end electrically connected to the negative input terminal, and another end electrically connected to the output terminal of the operation amplifier;
   a second resistance that has one end electrically connected to the output terminal of the operation amplifier, and another end electrically connected to the output terminal of the switch; and
   a third resistance that has one end electrically connected to the positive input terminal, and another end electrically connected to the other end of the second resistance.

9. The imaging apparatus according to claim 1,
   wherein the first extractor comprises:
   a PLL circuit that is arranged on the distal end side of the transmission channel, the PLL circuit being configured to generate a multiplied clock signal that has a higher frequency than a frequency of the superimposed signal in synchronization with one of a rising edge and a falling edge of the superimposed signal; and a restoring circuit that is arranged on the distal end side of the transmission channel, the restoring circuit being configured to restore the pulsed reference clock signal and the pulsed data signal included in the superimposed signal based on the superimposed signal and the multiplied clock signal.

10. The imaging apparatus according to claim 1, further comprising:

a parallel-to-serial converter that is arranged on the distal end side of the transmission channel, the parallel-to-serial converter being configured to perform parallel-to-serial conversion on the imaging signal and output the converted imaging signal to the transmission channel, wherein the first extractor further comprises:
  a PLL circuit that is arranged on the distal end side of the transmission channel, the PLL circuit being configured to generate a multiplied clock signal that has a higher frequency than a frequency of the superimposed signal to drive the parallel-to-serial converter in synchronization with one of a rising edge and a falling edge of the superimposed signal; and
  a restoring circuit that is arranged on the distal end side of the transmission channel, the restoring circuit being configured to restore the pulsed reference clock signal and the pulsed data signal included in the superimposed signal based on the superimposed signal and the multiplied clock signal.

11. The imaging apparatus according to claim 9,
wherein the imager comprises:
  a first chip comprising at least a pixel circuit configured to generate the imaging signal; and
  a second chip comprising at least the first extractor and the second extractor,
  wherein the first chip is laminated on the second chip.

12. The imaging apparatus according to claim 11,
wherein the imager is arranged at a distal end portion of an insertion portion to be inserted into a subject.

13. The imaging apparatus according to claim 12, further comprising:
an insertion portion to be inserted into a subject; and
a connector that is removably connected to the controller,
wherein the insertion portion comprises the imager, the first extractor, and the second extractor, and
wherein the connector comprises the superimposed signal generator.

14. An imaging system comprising:
an imager configured to generate an imaging signal by receiving light and performing photoelectric conversion on the light;
a controller configured to perform image processing on the imaging signal generated by the imager;
a transmission channel configured to connect the imager and the controller to transmit the imaging signal;
a superimposed signal generator that is arranged on a proximal end side of the transmission channel, the superimposed signal generator being configured to generate a superimposed signal by superimposing a pulsed data signal that is input from outside and a pulsed reference clock signal that is input from outside on negative voltage that is input from outside, and output the generated superimposed signal to the transmission channel;
a first extractor that is arranged on a distal end side of the transmission channel, the first extractor being configured to extract the pulsed data signal and the pulsed reference clock signal from the generated superimposed signal; and
a second extractor that is arranged on the distal end side of the transmission channel, the second extractor being configured to extract the negative voltage from the generated superimposed signal.

15. An imaging method comprising:
generating, by an imager, an imaging signal by receiving light and performing photoelectric conversion on the light;
performs, by a controller, image processing on the generated imaging signal;
transmitting the imaging signal from the imager to the controller;
generating, at a proximal end side of a transmission channel, a superimposed signal by superimposing a pulsed data signal that is input from outside and a pulsed reference clock signal that is input from outside on negative voltage that is input from outside;
outputting the generated superimposed signal to the transmission channel;
extracting, at a distal end side of the transmission channel, the pulsed data signal and the pulsed reference clock signal from the generated superimposed signal; and
extracting, at the distal end side of the transmission channel, the negative voltage from the generated superimposed signal.

* * * * *